United States Patent
Secrest et al.

(10) Patent No.: US 8,070,756 B2
(45) Date of Patent: Dec. 6, 2011

(54) POLYPECTOMY DEVICE AND METHOD OF USE

(75) Inventors: Dean J. Secrest, Concord, OH (US); K. Randall John, Chardon, OH (US); Christopher J. Kaye, Concord, OH (US)

(73) Assignee: U.S. Endoscopy Group, Inc., Mentor, OH (US)

( * ) Notice: Subject to any disclaimer, the term of this patent is extended or adjusted under 35 U.S.C. 154(b) by 592 days.

(21) Appl. No.: 11/404,345

(22) Filed: Apr. 14, 2006

(65) Prior Publication Data

US 2006/0235433 A1    Oct. 19, 2006

Related U.S. Application Data

(60) Provisional application No. 60/671,625, filed on Apr. 15, 2005.

(51) Int. Cl.
| A61B 17/24 | (2006.01) |
| A61B 17/26 | (2006.01) |
| A61B 10/00 | (2006.01) |

(52) U.S. Cl. ......... 606/113; 600/564; 600/565; 606/115
(58) Field of Classification Search .......... 600/562–572; 606/113, 114
See application file for complete search history.

(56) References Cited

U.S. PATENT DOCUMENTS

| 4,083,706 A | 4/1978 | Wiley |
| 4,146,019 A | 3/1979 | Bass et al. |
| 5,084,054 A * | 1/1992 | Bencini et al. ............... 606/113 |
| 5,279,548 A | 1/1994 | Essig et al. |
| 5,373,854 A * | 12/1994 | Kolozsi ......................... 600/562 |
| 5,417,697 A | 5/1995 | Wilk et al. |
| 5,423,830 A | 6/1995 | Schneebaum et al. |
| 5,441,503 A | 8/1995 | Considine et al. |
| 5,976,073 A | 11/1999 | Ouchi |
| 6,007,546 A | 12/1999 | Snow et al. |
| 6,068,603 A | 5/2000 | Suzuki |
| 6,142,956 A * | 11/2000 | Kortenbach et al. .......... 600/564 |
| 6,193,672 B1 | 2/2001 | Clement |
| 6,383,198 B1 | 5/2002 | Hamilton |

(Continued)

FOREIGN PATENT DOCUMENTS

EP    0 463 363 A2    2/1992

(Continued)

OTHER PUBLICATIONS

European Search Report from Application No. EP 06 11 2733, dated Jan. 12, 2007.

(Continued)

*Primary Examiner* — Max Hindenburg
*Assistant Examiner* — Adam Eiseman
(74) *Attorney, Agent, or Firm* — Calfee Halter & Griswold LLP

(57) ABSTRACT

A polyp removal tool and method of use is disclosed. The tool includes a main body, an elongated hollow conduit fixed to the body, a handle, a cable assembly, a suction assembly and an irrigation system. The handle is used to actuate a snare at the end of a cable for transecting of polypoid tissue. The suction assembly is used in pre-conditioning the tissue for cutting and in polyp retention after cutting. The irrigation system is included for tissue recovery after transection. The tool may include a screen for capture of tissue within the device.

8 Claims, 10 Drawing Sheets

U.S. PATENT DOCUMENTS

| | | | |
|---|---|---|---|
| 6,440,138 B1 * | 8/2002 | Reiley et al. .................... 606/79 |
| 2002/0049423 A1 | 4/2002 | Howell et al. |
| 2004/0059352 A1 | 3/2004 | Burbank et al. |
| 2004/0158127 A1 | 8/2004 | Okada |

FOREIGN PATENT DOCUMENTS

| | | |
|---|---|---|
| EP | 0 758 551 | 2/1997 |
| WO | WO 99/42041 | 8/1999 |
| WO | WO 99/51149 | 10/1999 |

OTHER PUBLICATIONS

Office Action from European Patent Application No. 06 112 733.8-1265 dated Feb. 19, 2009.

* cited by examiner

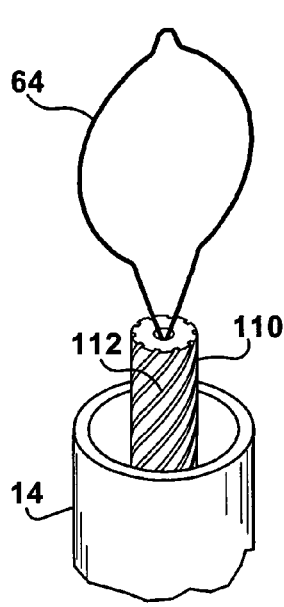
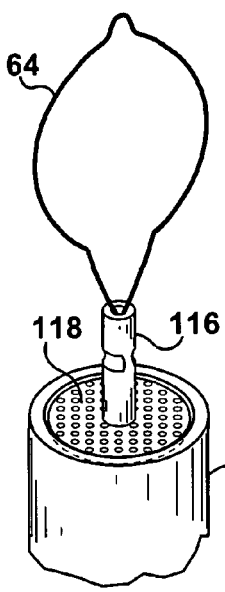
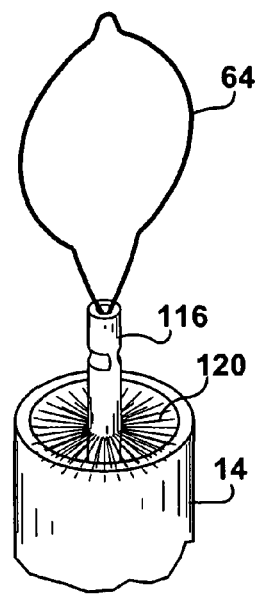
Figure 9　　Figure 10　　Figure 11
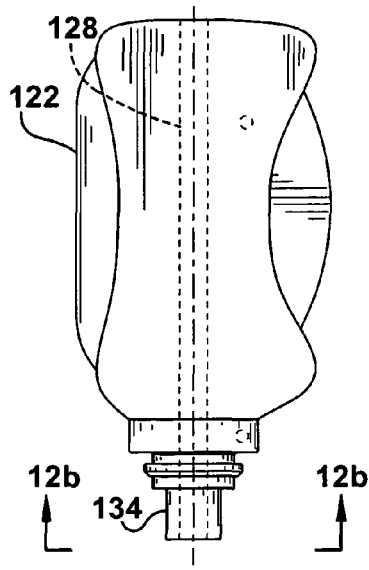
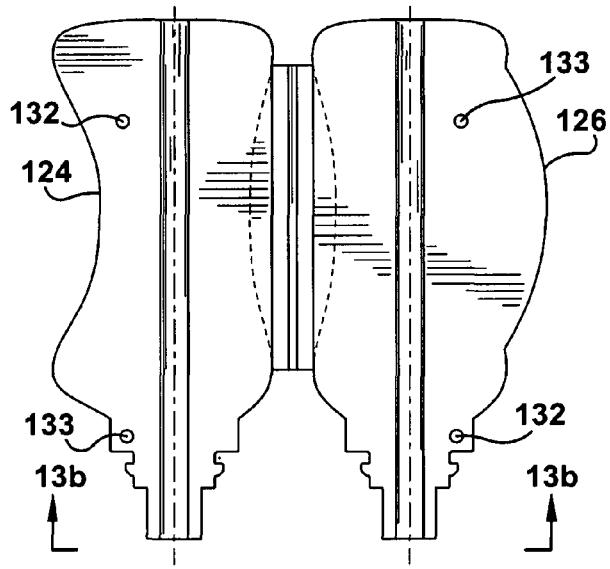
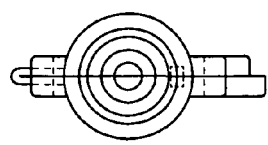
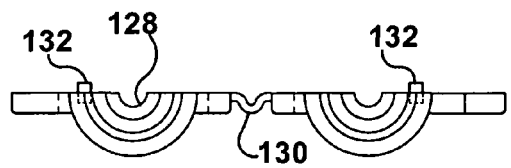
Figure 12a　　Figure 13a
Figure 12b　　Figure 13b

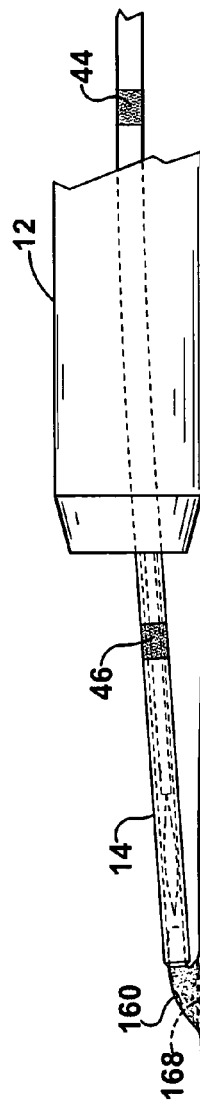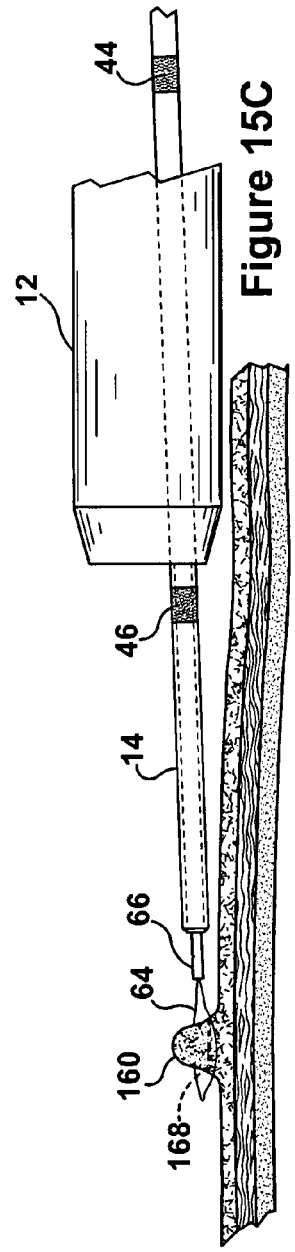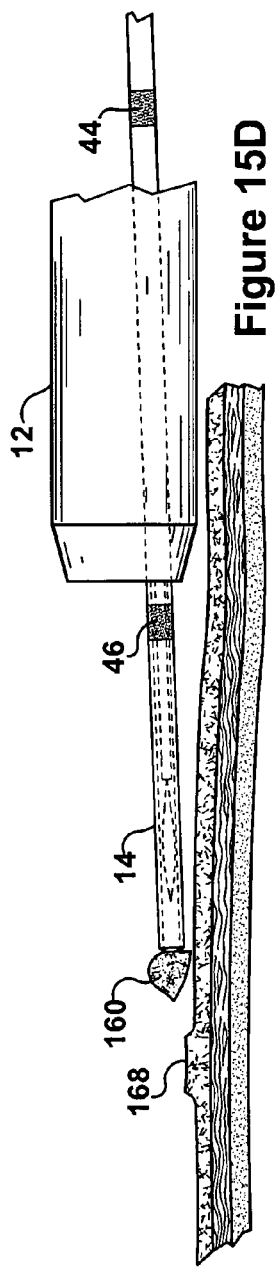
Figure 15A
Figure 15B
Figure 15C
Figure 15D

POLYPECTOMY DEVICE AND METHOD OF USE

CROSS-REFERENCE TO RELATED APPLICATIONS

This non-provisional application claims the benefit of U.S. Provisional Patent Application No. 60/671,625, entitled "Polypectomy Device and Method of Use," filed Apr. 15, 2005, which is hereby incorporated in its entirety.

FIELD OF THE INVENTION

The present invention relates to a device and method of use for removal of internal tissue such as, for example, a polyp.

BACKGROUND OF THE INVENTION

Removal of unhealthy internal tissue for diagnostic or other reasons by the use of various apparatus and techniques is known in the art. One such technique involves an endoscope. Endoscopic polypectomy is typically performed using electrocautery snares on polyps over 7 mm in diameter. Polyps under 3 mm are conventionally removed with a biopsy forceps. However, non-cautery or "cold guillotine polypectomy" is used for polyps that are between 3-7 mm. Diminutive polyps in this range are too small to use cautery in light of patient risks and are too large to conveniently biopsy.

A challenge with transecting a diminutive polyp is retrieving the relatively small specimen. Typically, the physician will use a separate suction trap and pull it through the biopsy channel of the endoscope. This technique is less than desired because the snare instrument must first be removed to provide a channel to perform the suction. While doing this exchange, the specimen may be lost. Certain other diminutive polyps are difficult to transect with a snare.

There remains a need in the art for a high-efficiency device that allows for multiple functions to be performed in the removal and recovery of a diminutive polyp, without requiring repetitive intubations of the instrument channel.

SUMMARY OF THE INVENTION

The present invention provides a new and improved polypectomy device and method of use thereof. The device is a single polypectomy device that offers suction, snaring and irrigation capabilities. The device includes a snare loop contained in a catheter which also has a suction source attached to it. Suction allows the physician to grasp on to the specimen and pull it either partially or completely inside the catheter. This technique allows for the specimen to be held at the tip of the catheter while the catheter is removed from the endoscope. In one embodiment, the device is for use in the instrument channel of an endoscope to remove a polyp sized 3-7 mm, a.k.a. a "diminutive polyp."

Further features and advantages of the invention will become apparent from the following detailed description made with reference to the accompanying drawings.

BRIEF DESCRIPTION OF THE DRAWINGS

FIG. 9 is a perspective view of yet another embodiment of the present invention, showing a connector at a distal end of the device;

FIG. 10 is a perspective view of yet another embodiment of the present invention, showing a screen at a distal end of the device;

FIG. 11 is a perspective view of yet another embodiment of the present invention, showing a brush at a distal end of the device;

FIG. 12a is a side view of yet another embodiment of the present invention, showing an alternative polyp removal tool in a closed position;

FIG. 12b is an end view of the polyp removal tool of FIG. 12a in a closed position;

FIG. 13a is a side view of the polyp removal tool of FIG. 12a, showing the tool in an open position;

FIG. 13b is an end view of the polyp removal tool of FIG. 12a in an open position;

FIG. 15a is a side view of a polyp on the mucosa layer of an intestinal wall;

FIG. 15b is a side view of the device of FIG. 1 being used on a polyp to pre-condition the polyp for removal;

FIG. 15c is a side view of the device of FIG. 1 being used to transect a polyp by snare retraction;

FIG. 15d is a side view of the device of FIG. 1 being used to secure a removed polyp by suction;

DETAILED DESCRIPTION OF THE INVENTION

The Detailed Description of the Invention merely describes preferred embodiments of the invention and is not intended to limit the scope of the specification or claims in any way. Indeed, the invention as described by the claims is broader than and unlimited by the preferred embodiments, and the terms in the claims have their full ordinary meaning.

A removal device for use with an endoscope to remove tissue from inside a patient is disclosed. Any discussion of a proximal end or distal end of the device or parts thereof is made in relation to an operator of the device. For exemplary purposes, the device will be discussed for use in a polypectomy procedure in removing a polyp from the mucosa layer of an intestinal wall. It should be understood by others with ordinary skill in the art that the device and method of use is not limited to this exemplary discussion.

Figure 1:
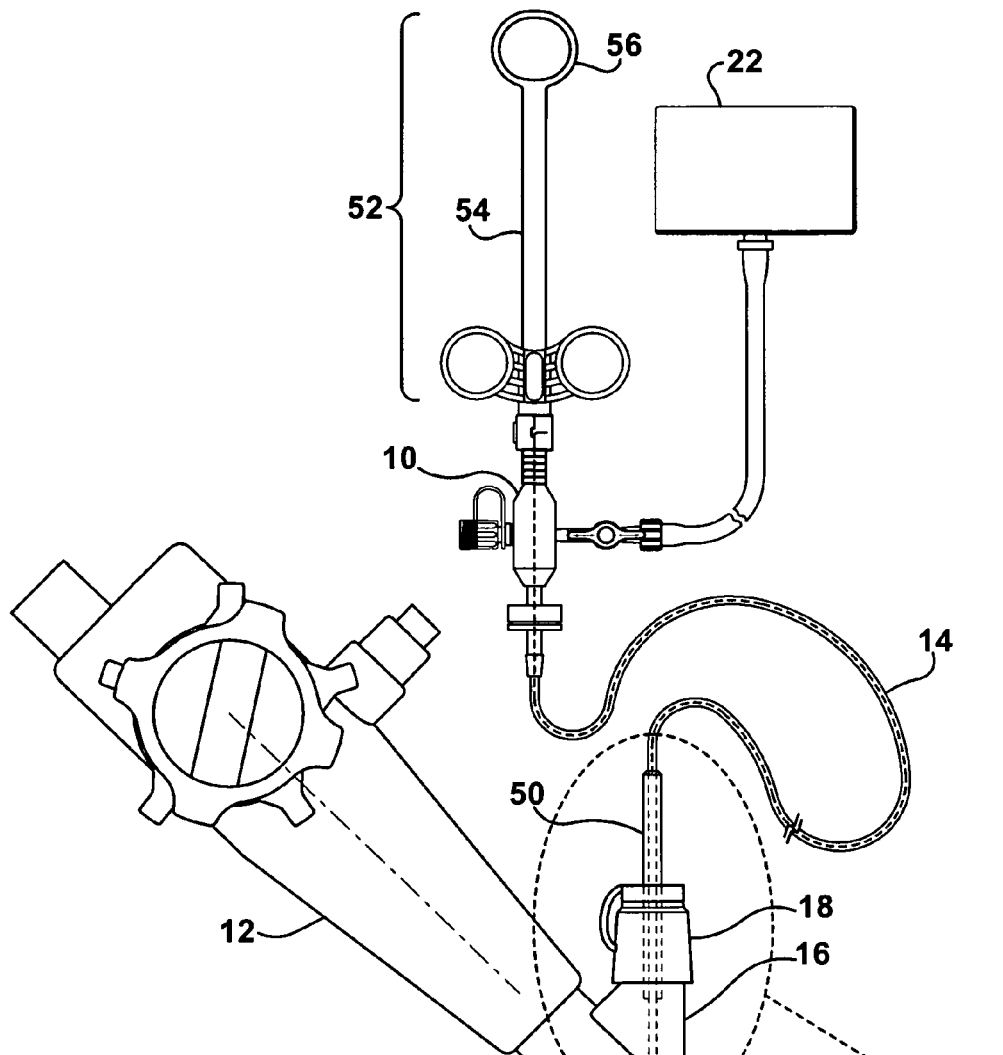
FIG. 1 is a perspective view of a polypectomy device constructed in accordance with an embodiment of the present invention, showing the device in use with an endoscope.
Figure 1:
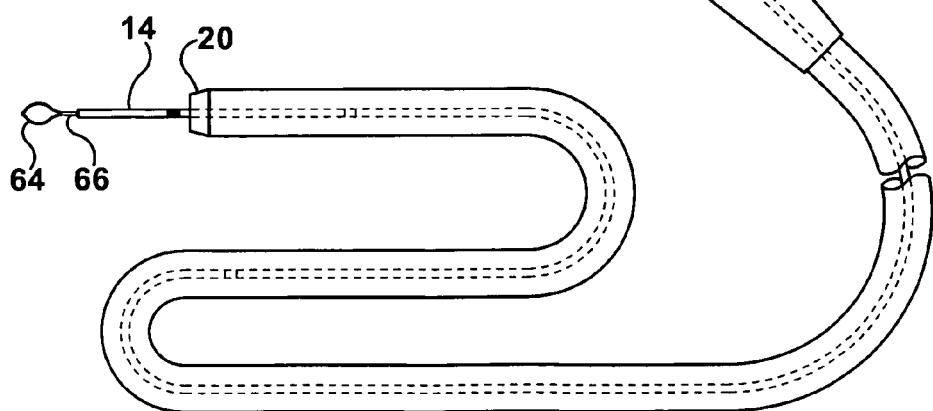

Referring now to the drawings, a polypectomy device constructed in accordance with an embodiment of the present invention is shown in FIG. 1. The device is illustrated in a functional position within a conventional endoscope. It should be understood that the use of the device is not limited to any specific endoscope design. The device includes cold-guillotine snaring, suction and irrigation capabilities in a single tool, eliminating the need for multiple tool insertions or multiple endoscope intubations during a single procedure. The device further offers flexibility in retaining and recovering transected polyps that are of a various size. Specifically, the device includes structure that accounts for the unpredictable size of a removed polyp.

Referring again to FIG. 1, a polypectomy device 10 is illustrated in an installed position within an endoscope 12. A physician can intubate a patient with the device 10 in this position to begin a polypectomy procedure. A conduit 14 of the device 10 is depicted inserted through a biopsy port 16 on an outer surface of the endoscope 12. The port 16 leads directly to an instrument channel of the endoscope. A biopsy valve 18 is installed on the port. A valve of this structure is shown and described in U.S. patent application Ser. No. 11/137,636, entitled "Irrigation Biopsy Inlet Valve," and filed on May 25, 2005. In the position shown, the conduit 14 is inserted through the instrument channel of the endoscope 12 to a position at or slightly beyond the distal end 20 of the endoscope 12. A suction source 22 is shown in fluid communication with the device.

Figures 2, 4:
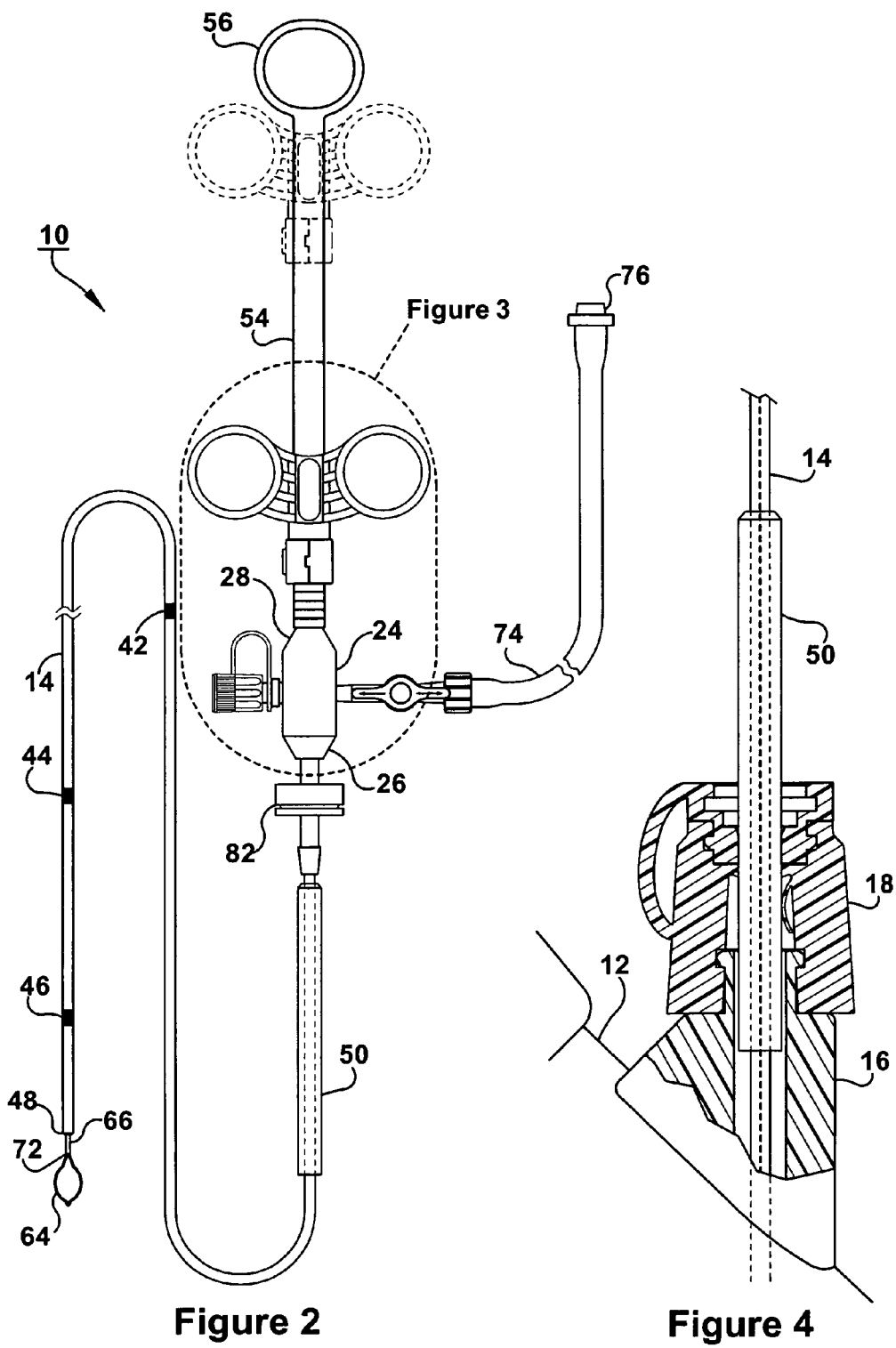
FIG. 2 is a side view of the device of FIG. 1.
FIG. 4 is an exploded view of a portion of the device and endoscope assembly of FIG. 1, showing a biopsy valve and polyp removal tool.
Figure 3:
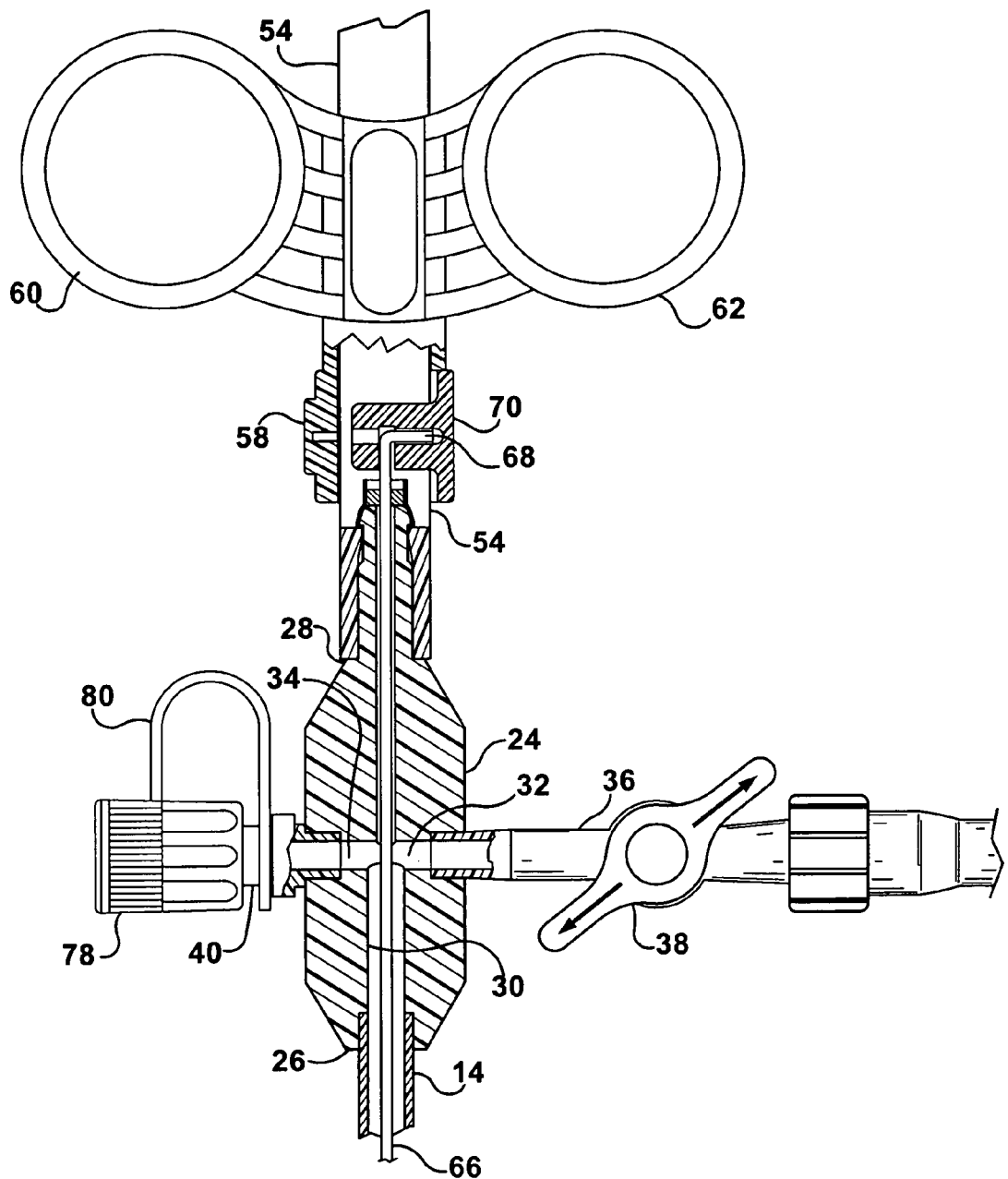
FIG. 3 is an exploded view, partially in section, of a portion of the device of FIG. 1, as shown as within the so designated circle in FIG. 2.

A view of the device 10 remote from an endoscope is shown in FIG. 2. In the embodiment shown, the device includes a main body 24 that includes structure inherent to the snaring, suction and irrigation capabilities of the device. The main body 24 is an elongated capsule-shaped housing with a distal end 26 and a proximal end 28. A cross-sectional view of the body 24 is shown in FIG. 3. An internal passage 30 extends longitudinally through the body 24 from the distal end 26 to the proximal end 28. Two secondary passages 32, 34 are connected to the main passage 30 to form a cross-shaped chamber within the body 24. A first secondary passage 32 extends from the main passage 30 to a rigid tube 36. To be discussed later in further detail, a stop cock 38 controls air flow through the rigid tube 36. A second secondary passage 34 extends from the main passage 30 to an irrigation port 40. Also to be discussed later in further detail, the irrigation port is used to provide a source of irrigation to the device 10.

As best shown in FIGS. 1-3, a conduit 14 is attached to the distal end 26 of the body 24. The exemplary conduit shown is a lengthy piece of single lumen, flexible TFE tubing. The conduit is adapted for insertion through the instrument channel of an endoscope. Tubing of various length, diameter and wall thickness can be utilized in the practice of the present invention. Further, a conduit having two separate lumens may be used. In a double lumen embodiment, one lumen houses the a cable and snare and the other houses a foam tipped pusher assembly. The foam tipped cable assembly allows suction to come therethrough toward a proximal suction source while still being able to push out the specimen after the device is removed from the endoscope.

As shown in FIG. 2, the conduit 14 includes length identifying indicia 42, 44, 46 relative to a distal end 48 of the conduit 14. The indicia shown are black rings imprinted on the outer surface of the conduit. It should be understood that indicia of other form and style may be used in the practice of this invention. The application of these indicia, i.e., a first mark 42, a second mark 44, and a third mark 46, will be discussed later in further detail.

A tissue removal tool 50 is positioned over the conduit 14. The tool 50 is a rigid cylindrical shaped tube and is slidable over the length of the conduit. In FIG. 1, the tool 50 is shown inserted into the biopsy valve 18. An exploded view the polyp removal tool 50 in an inserted position in shown in FIG. 4. The use of the tool 50 is optional and is only effective during certain segments of the polypectomy procedure. In fact, the tool 50 cannot stay in the valve 18 during the entire procedure because it would cause a continuous loss of insufflation air which is required to insufflate, or keep open, the intestine for visualization.

The snaring operation of the device 10 is controlled by a two-part sliding handle 52. A first handle member 54 is attached to the proximal end 28 of the body 24. The first handle member 54 is in the shape of an elongated shaft having a thumb ring 56 and is connected to the body 24. A second member 58 is slidably connected to the first member 54. The second member 58 includes two finger rings 60, 62. To be discussed later in further detail, a snare loop 64 at the distal end of the device 10 can be extended and retracted by manipulation of the handle second member 58 relative to the first member 54. In FIG. 1, the second member is shown in position adjacent the main body 24. In such a position, the snare loop is extended beyond the conduit. Referring now to FIG. 2, the second member is shown in phantom in a position remote from the main body 24. In such a position, the snare loop is retracted within the conduit. For example, a snare in a retracted position is shown in FIG. 15b.

Another component of the device 10 that is utilized in the snaring operation is a cable assembly. As shown in FIGS. 2-3, the cable assembly includes the snare loop 64 and a cable 66. The cable may be made of various suitable materials, such as for example, stainless steel. The snare loop 64 may be of various sizes, such as for example, constructed of a material from 0.010 to 0.018 inches in diameter. The snare loop 64 may be constructed of any suitable material, such as for example, a nickel titanium alloy such as Nitinol. As shown in FIG. 3, the cable 66 is positioned within the conduit 14 and the body passage 30. In an embodiment, the proximal last 6" of the cable 66 is covered by a hypodermic tube. The proximal end 68 of the hypodermic tube is "L-shaped" and is attached to the handle second member 58 by a snap cap 70. The distal end 72 of the cable is attached to the snare loop 64. It should be understood by others with ordinary skill in the art that various connection techniques and structure can be used at either end of the cable 66 in the practice of the present invention.

As discussed, the device 10 has suction capabilities for utilization during the polypectomy procedure. FIGS. 1-3 show a suction assembly for providing a suction force from the distal end of the conduit to a suction source 22. As best seen in FIG. 3, a rigid tube 36 is in communication with the internal passage 30. An actuator 38, such as a one-way valve as shown, controls flow of air from the rigid tube 36 to secondary tube 74. Suction is applied only intermittently in operation of the device 10. Thus, a valve is required. Other actuators can be used in the practice of the present invention, such as for example, a trumpet valve, or a trumpet valve with locking features. The tube 74 is constructed of a flexible plastic and has a connector 76 for attachment to the suction source 22. As shown, the suction assembly is in communication with the conduit 14 through the internal passage 30 of the body. It should be understood that the invention may be practiced with the suction assembly in direct communication with the conduit.

In operation of the device 10, an irrigation system may be used for recovery of removed polyps as required. Further, the irrigation system may be used to clean a work site during the procedure to provide a clear field of view. The irrigation system is in communication with the conduit and is used to supply a source of irrigation fluid in a direction toward the snare loop. As discussed and best shown in FIG. 3, the irrigation system includes an inlet port 40 attached to the body 24. The port provides access to second secondary passage 34, the passage 30, and ultimately the conduit 14. When not in use, the port can be sealed with a cap 78 that is secured to the device 10 by a tether 80. The cap 78 should be in place during operation of the suction assembly.

The irrigation assembly is used to recover a polyp that becomes embedded within certain portions of the device. For example, the device 10 includes a screen 82 disposed between the body distal end 26 and the conduit 14. As shown, the screen is adjacent the body but can be positioned at any location between the body and the conduit. Any removed polyp that is suctioned within the conduit may reach this screen under suction. After the device 10 is removed from the endoscope 12, an irrigation source can be connected to the port 40. An application of irrigation through the screen will force the polyp back out the distal end of the conduit.

Figure 5:
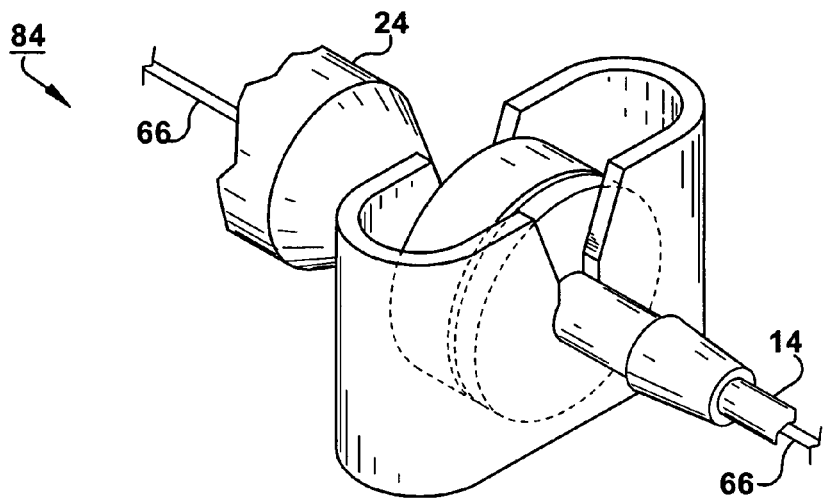
FIG. 5 is a perspective view of another embodiment of the present invention, showing a detachable polyp screen.
Figure 6:
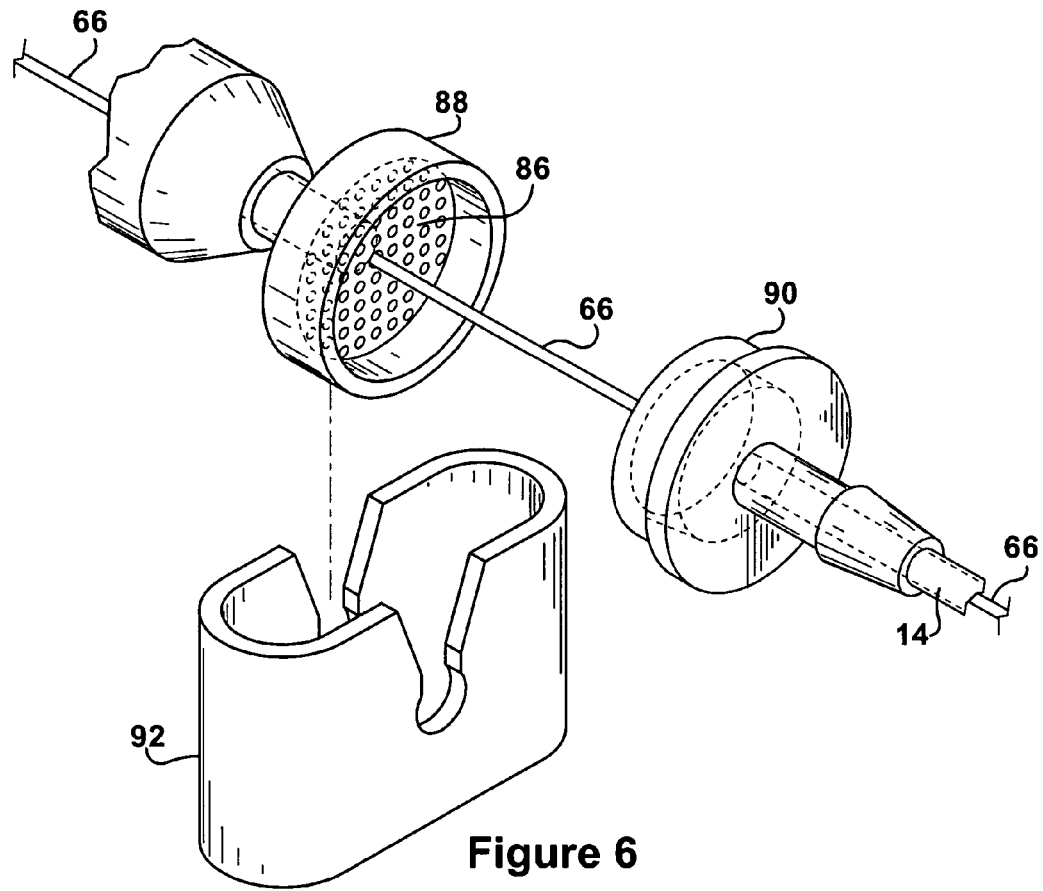
FIG. 6 is a perspective view of the detachable polyp screen of FIG. 5, showing a clip removed.

A perspective view of an alternative screen assembly 84 is shown in FIG. 5. The screen assembly 84 allows access to a screen 86 for removal of any trapped polyps. The assembly 84 include a female barb 88 and a male barb 90 held by a clip 92. FIG. 6 is a perspective view of the assembly 84 showing the clip 92 removed. The use of this assembly does not require irrigation to recover a polyp that has been suctioned within the conduit.

Figure 7:
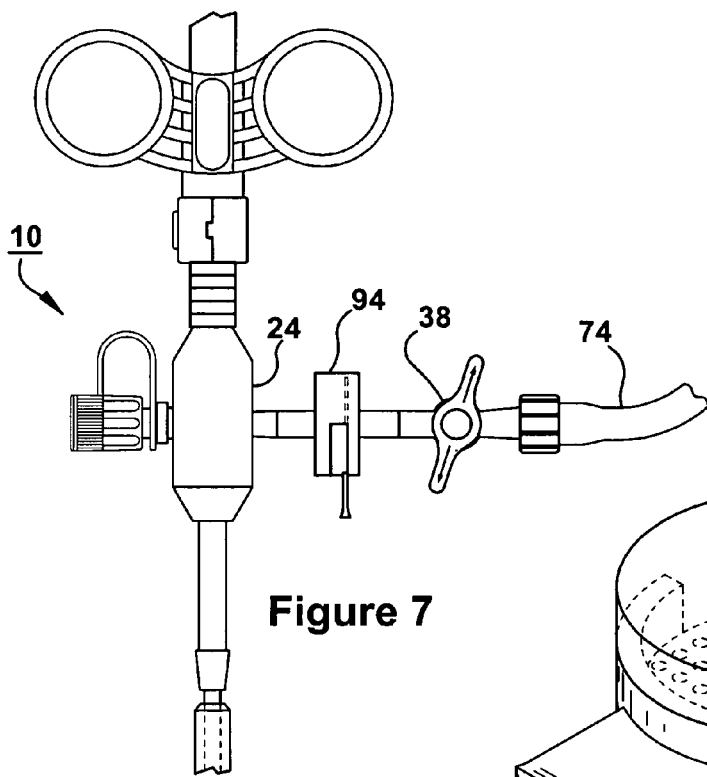
FIG. 7 is a side view of yet another embodiment of the present invention, showing a device having a removable polyp screen assembly.

Referring now to FIG. 7, a removable polyp screen assembly 84 is shown in a device 10. The screen assembly 94 is disposed between the main body 24 and the one-way stop valve 38. The assembly 94 has a removable screen that does not require in-line detachment.

Figure 8A:
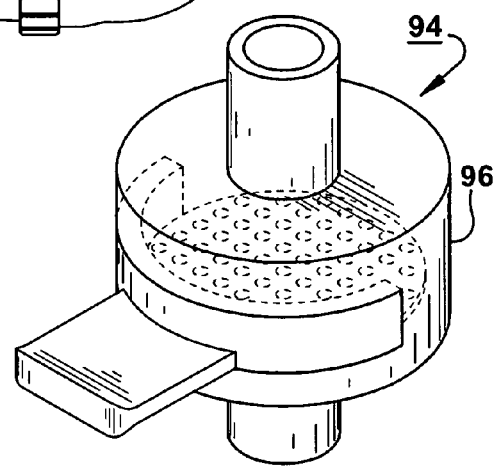
FIG. 8a is a perspective view of the removable polyp screen assembly of FIG. 7.
Figure 8B:
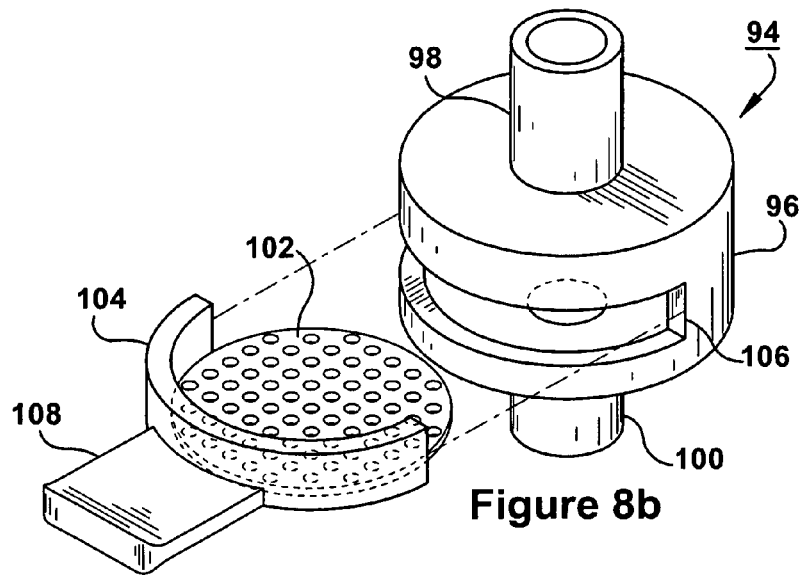
FIG. 8b is a perspective view of the polyp screen of FIG. 7 in a removed position.

A perspective view of the removable polyp screen assembly 84 is shown in FIG. 8a. The assembly includes a cylindrical-shaped base 96 with input and output suction ports 98, 100, respectively. As air is suctioned through the assembly, any polyp tissue is trapped on a screen 102. FIG. 8b is a perspective view of the polyp screen 102 in a removed position. The screen 102 is mounted to a cartridge 104 that is insertable into a correspondingly shaped slot 106 within the base 96. The cartridge 104 includes a finger tab 108 for ease of use.

Removed polyps of small size can be trapped by other structure in the practice of the present invention. In yet another embodiment of the present invention, a tissue trap is fixed to the cable 66 adjacent the distal end of the conduit 14. FIG. 9 is a perspective view of a connector 110 at a distal end of the device 10. As shown, the connector secures the snare loop 64 to the cable 66 (not shown). The diameter of the connector is greater than a diameter of the cable, such that a polyp of a certain size cannot be suctioned between the connector and the inner wall of the conduit 14. Grooves 112 are included on a surface of the connector 112 to promote suction forces.

Two other alternative tissue traps are shown in FIGS. 10-11. FIG. 10 is a perspective view of connector 116 at a distal end of the device 10. A screen 118 is attached to the connector for trapping tissue prior to entering the conduit 14. In FIG. 11, a brush 120 is attached to the connector 116.

As discussed and best shown in FIG. 4, a polyp removal tool 50 can inserted into the biopsy valve 18 to assist in polyp removal from the endoscope 12. An alternative polyp removal tool 122 is shown in FIGS. 12a-13b. The polyp removal tool includes two hinged portions 124, 126 and defines a passage 128. A diameter of the passage is equal to or larger than the diameter of the conduit 14. As such, the tool 122 can be positioned over the conduit 14 and, in such a position, is slidable over a length of the conduit. To position the tool 122 in place, the two portions 124, 126 are rotated about a hinge 30 to a closed position shown in FIGS. 12a and 12b. Protruding tabs 132 are press fit in place into corresponding holes 133 to secure the tool in place with the conduit within the passage 128. A plug 134 is sized for a press-fit insertion into the biopsy valve 18.

Figure 14:
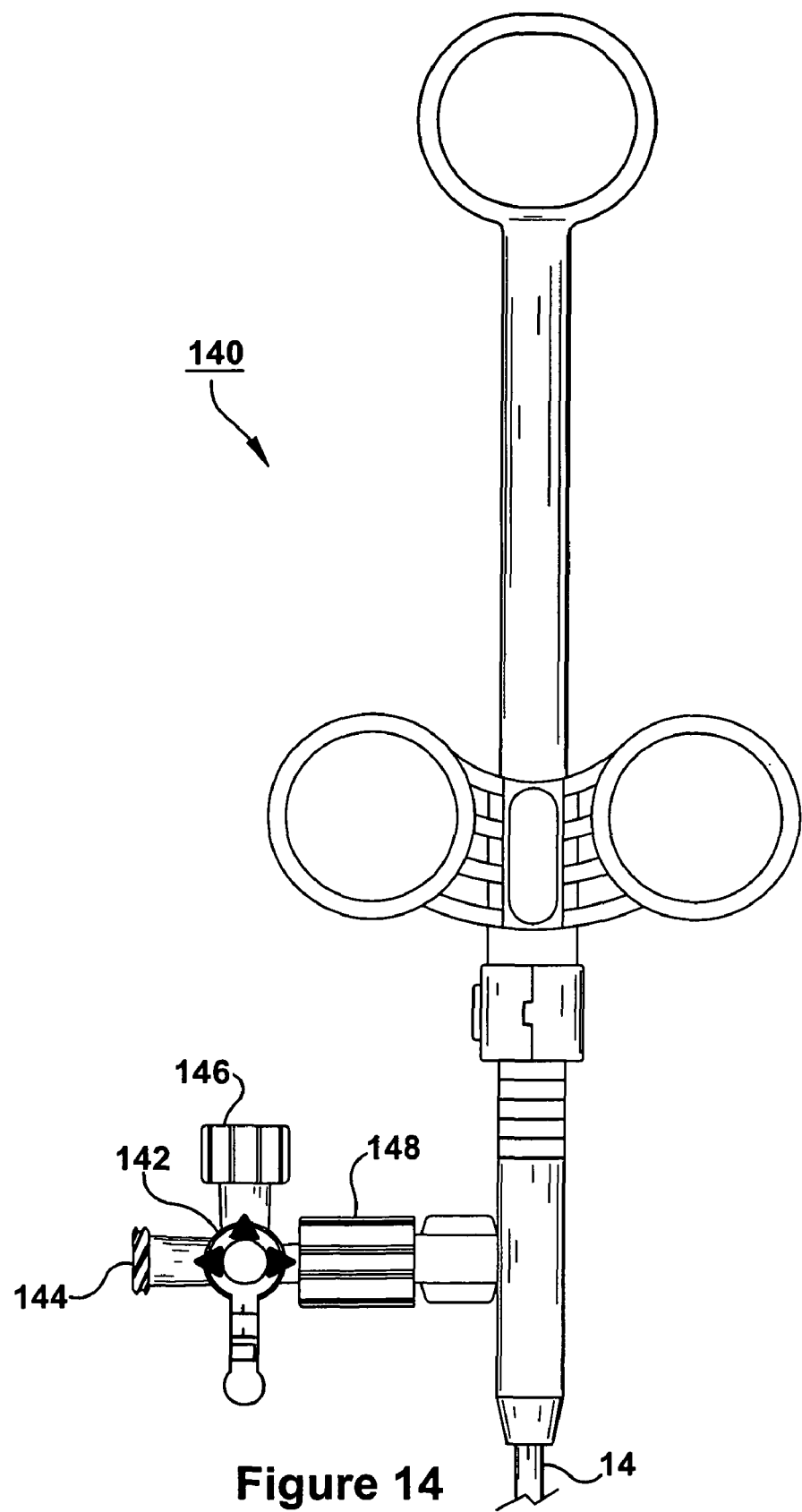
FIG. 14 is a side view of yet another embodiment of the present invention, showing a device having a three position suction and irrigation valve.

Another embodiment of the present invention is illustrated in FIG. 14. A device 140 is shown with an actuator 142 that incorporated both suction and irrigation controls. The actuator provides access from either a suction port 144 or an irrigation port 146 to the conduit 14 through a connection 148. The stop valve 142 shown has essentially three operating positions. A first position allows essentially no flow in either direction through the connector 144. A second position allows air flow through the connection 148 toward the suction port. A third position allows essentially no air flow toward the suction source but allows irrigation liquid flow from the irrigation port 146 toward the conduit 14.

A method of use of the device 10 for removing a polyp from a gastro-intestinal wall of a patient will now be discussed. The series of FIGS. 15a-15d illustrate an exemplary method for removal and recovery of a polyp. It should be understood by others with ordinary skill in the art that other removal methods can be undertaken in the practice of the present invention. Referring to FIG. 15a, a side view of a polyp 160 on an intestinal wall is shown. Specifically, the polyp is formed on the mucosa layer 162, above the submucosa layer 164 and muscularis 166. As discussed, diminutive polyp are difficult to remove and recover. Further complicating such a procedure, a polyp may grow back if not transected at its base. To minimize these problems, the suction capabilities of the device 10 can be used to pre-tent or "tee up" the polyp prior to use of the snare. By lifting the polyp away from the internal tissue wall, the physician can more easily transect a target line 168 at or near the base of the polyp, and decrease the likelihood of the polyp growing back.

Referring now to FIG. 15b, an intubated endoscope 10 is shown adjacent the mucosa layer 162. A conduit 14 is shown extending from the instrument channel to a location adjacent a polyp 160 that has been identified for removal. An operator next applies suction to a polyp 160. As a consequence of the suction, the polyp is pulled away from the mucosa layer 162 toward the distal end of the conduit 14. As seen in FIG. 15c, this suctioning technique has the advantageous effect of pre-conditioning the polyp 160 for removal by transection along its base 168. While the polyp is in the pre-conditioned position, a snare loop 64 is extended around the circumference of the polyp 160 as shown in FIG. 15c.

As discussed, the snare loop 64 is operable from an extended position to a retracted position by manipulation of the handle 52. Next, the snare is retracted to transect the polyp along its base. In FIG. 15d, the snare is shown in a retracted position after the polyp has been transected at its base 168. In the exemplary procedure shown, the polyp 160 is larger in diameter than the inner diameter of the conduit. Thus, the polyp is retained under suction at a distal end of the polypectomy device 10 as shown. Polyps of smaller size may be retained just inside the distal end of the conduit or at other places within the device, such as for example, a screen, and ultimately recovered by irrigation or screen detachment or screen removal as previously discussed.

Referring again to FIG. 15*d*, the application of suction allows the physician to grasp on to the polyp 160 and either pull it completely inside the conduit or partially inside the conduit. This recovery method allows for the polyp to be held at the tip of the conduit while the conduit is removed from the endoscope. However, because the shape of the polyp is highly variable, the reliability of pulling the polyp completely inside may vary. In fact, recovery problems can be caused if the specimen is not completely pulled inside the catheter. When extubating the conduit out of the biopsy inlet valve, the tightness of the valve opening can tend to strip the specimen away from the catheter. Consequently, the polyp may stay inside the valve or be lost in the instrument channel of the endoscope.

Figure 16:
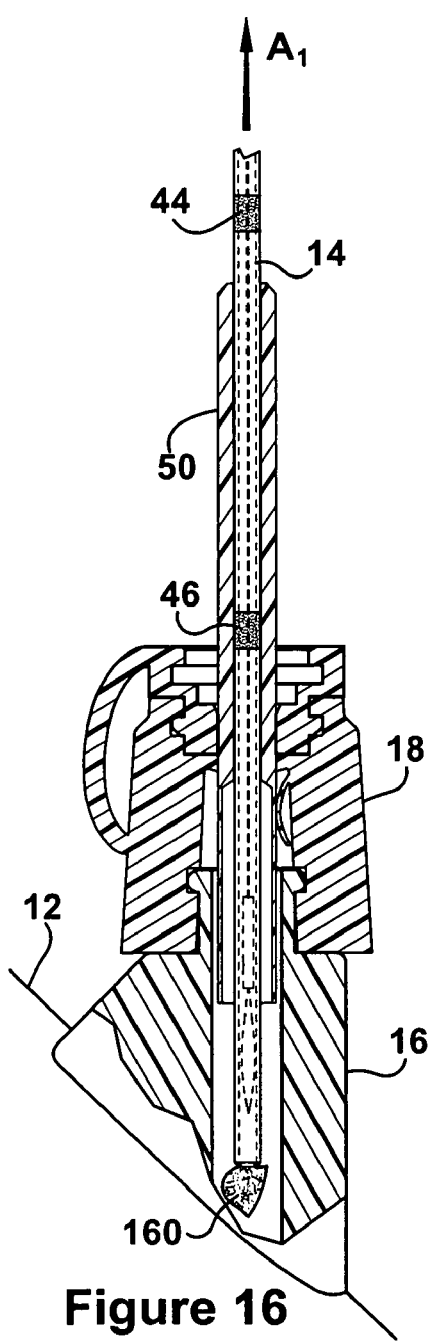
FIG. 16 is a cross-sectional view of a conduit being removed from a biopsy valve, showing a polyp secured to an end of the conduit.
Figure 17:
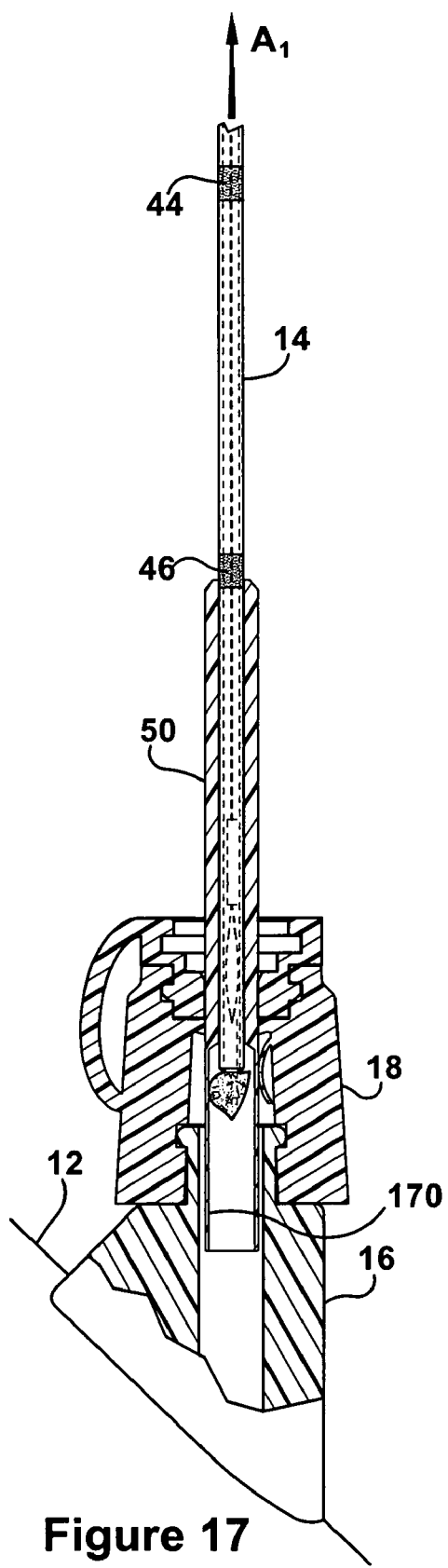
FIG. 17 is a cross-sectional view of a conduit being removed from a biopsy valve, showing the polyp within a polyp removal tool.
Figures 18, 19:
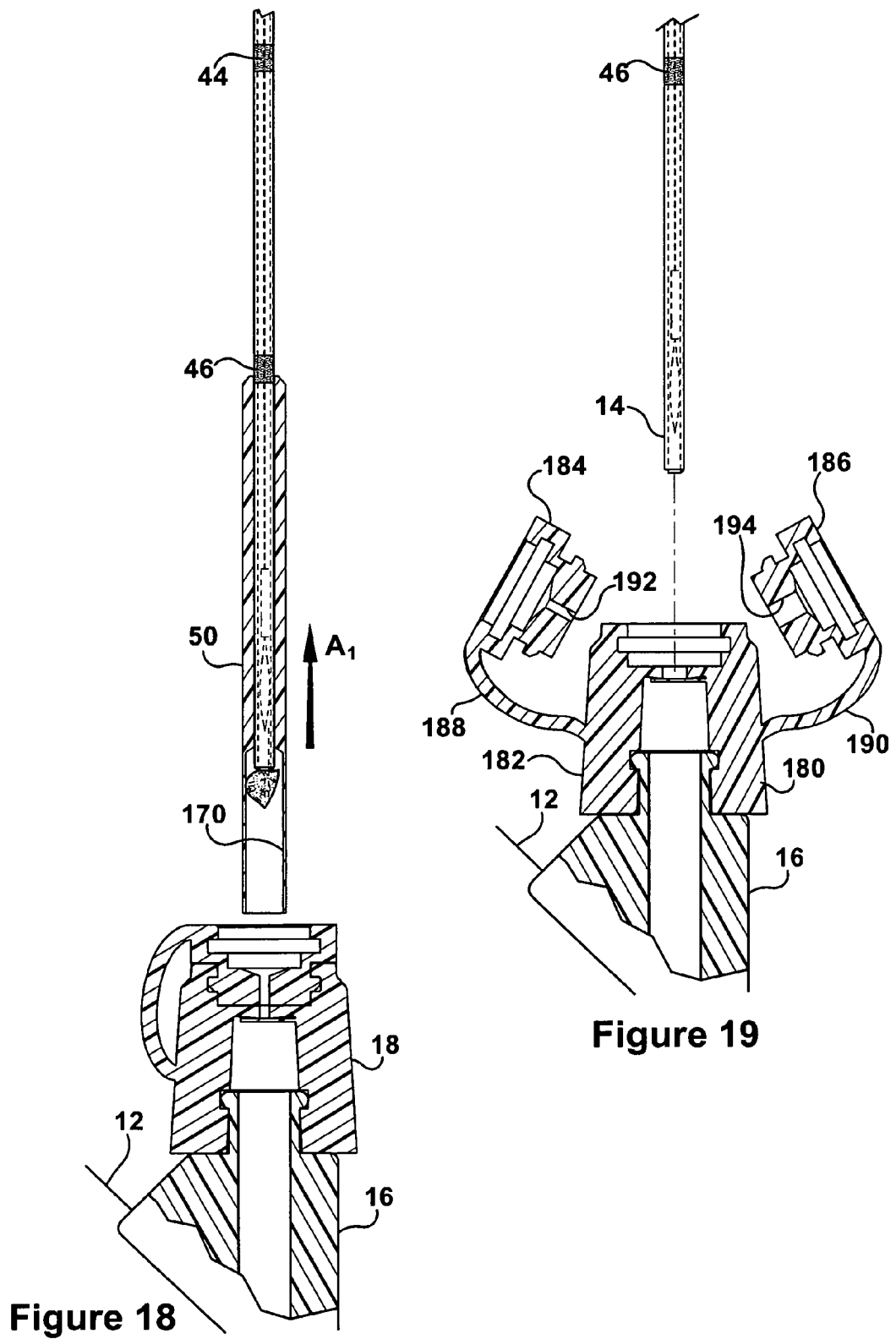
FIG. 18 is a cross-sectional view of a conduit being removed from a biopsy valve, showing the polyp removal tool disposed remote from the biopsy valve.
FIG. 19 is a cross-sectional view of an alternative biopsy valve.

A method of removing a polyp under suction or otherwise retained at a distal end of the conduit 14 is shown in FIGS. 16-18. First referring again to FIG. 15, a polyp 160 is shown held under suction to the distal end of a conduit 14. Alternatively, the polyp may be suctioned to a location just within the conduit 14. If the polyp is embedded in a tissue trap or otherwise engaged inside the distal end of the conduit, suction may not be required. Regardless, the recovery method depicted in FIGS. 16-18 begins with an operator withdrawing the conduit 14 through the biopsy valve 18 in a direction $A_1$. The withdraw speed can vary based on the operator's skill and preference. During withdraw of the conduit, a first mark 42 (not shown) acts as a warning to the operator as it appears from the removal tool 50. In other words, the appearance of the first mark 42 beyond the tool 50 signals the operator to slow the withdrawal speed in light of the approaching distal end of the conduit 14.

The appearance of the first mark 42 also has other significance. At this time, an operator may insert the optional polyp removal tool 50 into the biopsy valve 18. The tool 50 widens the biopsy valve and reduces the likelihood of the polyp 160 being dislodged in the valve.

After the withdraw speed is slowed, the operator next watches for the appearance of the second mark 44 beyond the tool 50. FIG. 16 is a cross-sectional view of a conduit in such a position as it is being removed from the biopsy valve 18. As shown, the tool 50 is inserted into the valve 18 to define a removal path. The appearance of the second mark 44 warns the operator that the polyp 160 is relatively near the tool 50 and caution is mandated.

Exercising appropriate care, an operator proceeds to withdraw the conduit 14 through the biopsy valve 18 in a direction $A_1$ until the appearance of the third mark 46. This position is illustrated in FIG. 17. The polyp 160 now rests within a polyp retaining cavity 170 defined within the polyp removal tool 50. As depicted in FIG. 18, an operator can grasp the outside of the tool 50 and pull the tool and the conduit together in the direction $A_1$ until the tool disengages with the biopsy valve 18. The polyp can now be safely recovered without risk of loss. Recovery can be achieved by removing the conduit from the tool and either merely discontinuing any suction of the polyp, or applying an appropriate amount of irrigation to dislodge the polyp 160.

As discussed, the present invention embodies other polyp recovery methods. The polyp can be captured on a screen. The irrigation capabilities of the device 10 can be used to flush out such a polyp toward and out of the distal end of the conduit. Further, the screen can be part of an assembly that can be disengaged to provide access to a polyp. Further, a cartridge containing a screen can be removed to provide access to a polyp. In these and other situations in which a physician was certain the polyp was within device 10, a physician can merely pull the conduit 14 out straight from the valve 18 without use of the tool 50.

FIG. 19 shows an alternative biopsy valve 180 that can also be utilized as a polyp removal tool. The valve as shown is integrally molded to include a body 182 and two separate caps 184, 186. A first cap 184 is held adjacent the body 182 by a first tether 188. Likewise, a second cap 186 is held adjacent the body 182 by a second tether 190. The first cap 184 defines a slit 192. In one embodiment, the slit 192 is narrower than a diameter of a passage 194 defined by the second cap 186. The slit 192 allows the valve 180 to be used for a variety of endoscopic procedures requiring a seal at the cap 184. The passage 194 allows for insertion of a polyp removal tool. The size of the slit 192 and passage 194 may vary in size and in relative size to each other in the practice of the present invention.

While several embodiments of the invention has been illustrated and described in considerable detail, the present invention is not to be considered limited to the precise constructions disclosed. Various adaptations, modifications and uses of the invention may occur to those skilled in the arts to which the invention relates. It is the intention to cover all such adaptations, modifications and uses falling within the scope or spirit of the claims filed herewith.

What is claimed is:

1. A tissue removal tool for use with an endoscope, said tool comprising:
   a. a main body having a distal end and a proximal end, and defining a passage between said distal end and said proximal end;
   b. a conduit having a proximal end communicably attached to said passage at a distal end of said body;
   c. a handle assembly attached to said body proximal end, said handle having a first member connected to said proximal end of said body and a second member slidably connected to said first member in a co-axial relationship, wherein said second member is movable relative to said main body and to said first member;
   d. a cable assembly positioned within said conduit and said passage, said cable assembly comprising:
      i. a snare; and
      ii. a cable having a first end attached to said handle second member and a second end fixed to said snare, wherein said cable is movable relative to said main body;
   e. a suction assembly in communication with said passage via a port on said main body between said distal end and said proximal end, said suction assembly comprising a tube attachable to said suction source, and an actuator for control of air flow through said tube toward said suction source; and
   f. a screen disposed between said suction assembly actuator and said snare;
   g. wherein a radial space between an outer surface of said cable and an inner surface of said conduit defines a passageway in communication with said port.

2. The tissue removal tool of claim 1 wherein said screen is detachable absent disassembly of said suction assembly.

3. The tissue removal tool of claim 1 further comprising a polyp removal tool positioned over said conduit and slidable over said conduit, wherein said polyp removal tool comprises two hinged portions.

4. The tissue removal tool of claim 1 further comprising a polyp removal tool positioned and slidable over said conduit, wherein said polyp removal tool defines a polyp retaining cavity.

5. A polypectomy device for use with a flexible endoscope comprising:
- a main body having a distal end, a proximal end, and a side port, and defining an internal passage between said distal end, said proximal end, and said side port;
- a conduit fixed to said body distal end and operably configured to be flexibly insertable into an instrument channel of the flexible endoscope;
- a handle attached to said body proximal end, said handle having a first member connected to said proximal end of said body and a second member slidably connected to said first member and disposed between a proximal end of said first member and a distal end of said first member, wherein said second member is movable relative to said main body;
- a cable assembly at least partially positioned within said conduit and said passage, said cable assembly comprising a snare loop movable by said handle second member relative to said main body for transecting a polyp and a cable having a proximal end attached to said handle second member and a distal end attached to said snare loop;
- wherein a radial space between an outer surface of said cable and an inner surface of said conduit defines a passageway in communication with said port;
- a suction assembly in communication with said conduit, said suction assembly comprising a tube attached to said side port and a valve for control of air flow from said conduit toward a suction source through said tube; and
- a tissue trap assembly fixed to said tube at a location proximal to said side port;
- wherein said tissue trap assembly includes a screen removable without detachment of the tissue trap assembly.

6. The polypectomy device of claim 5 wherein said tissue trap assembly is disposed between said side port and said valve.

7. The polypectomy device of claim 5 wherein said handle second member is oriented co-axially to said handle first member.

8. The tissue removal tool of claim 7 wherein said conduit defines a double lumen, wherein said cable is positioned in a first lumen and said suction assembly is in communication with a second lumen.

* * * * *